US008677990B2

(12) United States Patent
    Gabriel

(10) Patent No.: US 8,677,990 B2
(45) Date of Patent: Mar. 25, 2014

(54) ENDO-TRACHEAL INTUBATION DEVICE WITH ADJUSTABLY BENDABLE STYLET

(75) Inventor: Sabry Gabriel, Lizella, GA (US)

(73) Assignee: Syncro Medical Innovations, Inc., Lizella, GA (US)

( * ) Notice: Subject to any disclaimer, the term of this patent is extended or adjusted under 35 U.S.C. 154(b) by 126 days.

(21) Appl. No.: 13/066,928

(22) Filed: Apr. 28, 2011

(65) Prior Publication Data

US 2011/0265789 A1    Nov. 3, 2011

Related U.S. Application Data

(60) Provisional application No. 61/343,413, filed on Apr. 28, 2010.

(51) Int. Cl.
    *A61M 16/00*    (2006.01)
(52) U.S. Cl.
    USPC ............. 128/200.26; 128/207.14; 600/146; 604/164.01; 604/170.02
(58) Field of Classification Search
    USPC ............ 128/200.26, 207.14, 207.15, 207.18; 600/114, 120, 139–149; 604/164.04, 604/170.01, 170.02
    See application file for complete search history.

(56) References Cited

U.S. PATENT DOCUMENTS

| | | | |
|---|---|---|---|
| 4,529,400 A * | 7/1985 | Scholten | 604/528 |
| 5,327,881 A * | 7/1994 | Greene | 600/120 |
| 5,498,231 A * | 3/1996 | Franicevic | 600/190 |
| 5,636,625 A * | 6/1997 | Miyagi et al. | 128/200.26 |
| 5,676,635 A * | 10/1997 | Levin | 600/120 |
| 5,733,242 A * | 3/1998 | Rayburn et al. | 600/120 |
| 5,758,656 A * | 6/1998 | Schroeder | 600/585 |
| 5,791,338 A * | 8/1998 | Merchant et al. | 128/200.26 |
| 5,840,013 A * | 11/1998 | Lee et al. | 600/114 |
| 6,146,402 A * | 11/2000 | Munoz | 606/194 |
| 6,319,195 B1 * | 11/2001 | Nakaichi et al. | 600/120 |
| 6,539,942 B2 | 4/2003 | Schwartz et al. | |
| 6,929,600 B2 * | 8/2005 | Hill | 600/120 |
| 7,458,375 B2 * | 12/2008 | Schwartz et al. | 128/207.14 |
| 2002/0108610 A1 * | 8/2002 | Christopher | 128/200.26 |
| 2004/0059257 A1 * | 3/2004 | Gaber | 600/585 |
| 2004/0215061 A1 * | 10/2004 | Kimmel et al. | 600/179 |
| 2008/0017195 A1 * | 1/2008 | Yoshida | 128/200.26 |
| 2009/0318769 A1 * | 12/2009 | Tenger et al. | 600/199 |
| 2010/0108060 A1 * | 5/2010 | Pecherer et al. | 128/200.26 |
| 2011/0120458 A1 * | 5/2011 | Schwartz et al. | 128/200.26 |

* cited by examiner

*Primary Examiner* — Justine Yu
*Assistant Examiner* — Christopher Miller
(74) *Attorney, Agent, or Firm* — Withers & Keys, LLC (57) ABSTRACT

An inexpensive, endo-tracheal intubation device is disclosed. Methods of making and using the inexpensive, endo-tracheal intubation device are also disclosed.

20 Claims, 13 Drawing Sheets

ENDO-TRACHEAL INTUBATION DEVICE WITH ADJUSTABLY BENDABLE STYLET

CROSS-REFERENCE TO RELATED APPLICATION

This application is a non-provisional application of the earlier filed provisional application, Ser. No. 61/343,413, filed on Apr. 28, 2010, and claims the benefit of priority of the filing date of Apr. 28, 2010, pursuant to 35 U.S.C. Sec. 119(e).

FIELD OF THE INVENTION

The present invention relates generally to medical devices designed to improve airway tube placement and, more specifically, to such devices which allow a medical practitioner to insert an airway tube rapidly and properly in a patient's trachea.

BACKGROUND OF THE INVENTION

In a medical emergency, it is frequently necessary for the medical practitioner to insert a breathing tube into the patient's trachea so that he or she can be ventilated. The tube must enter the larynx and pass through the opening between the vocal cords. Care must be taken during insertion to prevent the tube from entering the esophagus.

Some patients present more difficult airway access than others. Medical experts have classified airways into four different types. Type I is easily accessible and type IV is the most difficult. Airways need to be protected in unconscious patients, as well as in those of motor vehicle accident victims who may have suffered an unknown fracture of the cervical spine. This presents a special challenge to the medical practitioner. In such situations, if one were to extend the neck in the usual fashion, that is, in such a way that one can visualize the vocal cords by using a direct laryngoscope in order to insert the endo-tracheal tube, one could injure the spinal cord, causing severe paralysis or even death. Moreover, endo-tracheal tube insertion must be accomplished in less than 4 minutes to avoid brain death. Prolonged intubation procedure time can result in various degrees of brain injury.

Accidental placement of an endo-tracheal tube, whether it is inserted nasally or orally, in the esophagus rather than in the trachea is a possibility because of the natural curvature of the orpharynx. Such placement can result in patient hypoxia, varied degrees of brain damage and/or death.

The shape of a patient's throat varies widely from one individual to the next. In some patients, the vocal cords can be seen on visual inspection and it is relatively easy to insert ah intubation device. However, in other patients, the vocal cords are completely hidden from view, making insertion of the intubation device difficult. Often it is helpful to extend the patient's head backward as far as possible to increase the medical practitioner's view of the vocal cords; but such an approach cannot be used if the patient has suffered a neck injury and has to be made immobile in order to prevent further damage.

In practice then, physical and anatomical variations among patients can make it difficult for a medical practitioner to clearly identify a particular individual's vocal cords. Unless they can be properly identified, however, they may be damaged during ah intubation procedure. To address this heed, Schwartz et al. (U.S. Pat. No. 6,539,942) disclosed a tubular endotracheal device, capable of being flexed into a L-shape and through which a conventional imaging device, such as a nasopharyngoscope, is inserted centrally, so as to allow for direct visualization of the vocal cords.

Unfortunately, this prior art combination is too costly to be disposed of after a single patient use; and the probability of infectious materials being transmitted from one patient to another is high—especially during a medical emergency in which more than one airway-compromised patient is involved and the same imaging device must be reused immediately.

SUMMARY OF THE INVENTION

The object of this invention is to provide a disposable, inexpensive-to-manufacture endo-tracheal tube placement device which includes components useful for visualizing key anatomical structures which a medical practitioner encounters in the course of gently pushing a portion of a tube placement device between a patient's vocal cords and into his trachea, the portion so pushed being encased in the endo-tracheal tube prior to its insertion into the patient's airway, said portion being adjustably bendable in such a way that the endo-tracheal tube can be inserted into the patient's trachea even when visualization of the anatomical structures is difficult because of the shape of the patient's throat and/or because of injury.

A further object is to provide an endo-tracheal intubation device which paramedical personnel, after a brief training exercise in its applications, can safely use to assist a patient experiencing a compromised airway.

A still further object is to provide a one-handed endo-trachel intubation device which emergency medical technicians can use in the field, freeing up one of the hands of the individual performing the intubation procedure so that he can use his free hand to support the patient's head and/or otherwise assist in the intubation process.

In combination with an endo-tracheal tube which, like those well-known in the prior art, is typically made of a flexible, medical grade PVC material with substantial resistance to collapse, the improved endo-tracheal intubation device, according to the present invention, includes a stylet with a bendable, substantially tubular element, an elongated stylet holder, and a bell crank pivotally mounted thereon which is connected to the stylet by a flexible wire. Fabricated of a hollow, semi-rigid, medical grade plastic material which is generally circular in transverse cross-section, the tubular element encases a portion of the flexible wire, which not only extends lengthwise through the tubular element but also protrudes therefrom. In assembled relation, one end of the tubular element is slip-fitted, pinched or otherwise firmly held in place within a cylindrically-shaped void defined by interior walls of the stylet holder. Also so defined by its interior walls is a through passageway which communicates with the cylindrically-shaped void and through which the flexible wire passes enroute to its connection with the bell crank.

Distal from the stylet holder, the end of the tubular element is covered by a metal cap which preferably also encases a disk to which the flexible wire is affixed and on which a LED light is mounted in such a way that it protrudes outwardly from the stylet's tip. Bright enough to be seen through the skin of a patient's neck in a darkened setting, the LED light allows the user to track the endo-tracheal tube's advancement along the patient's airway, as well as to visualize his vocal cords. In the preferred embodiment, the LED light is powered by at least one battery housed within the stylet holder and is activated by a sliding, on-and-off switch mounted thereon.

Proximate with the metal cap, the stylet's tubular element is scored in such a way that it can be bent in a controlled manner by tensioning the flexible wire, without disturbing electrical wires, connecting the LED light to the battery, which also run through the tubular element. In the preferred embodiment, the scored portion of the tubular element defines a series of spaced apart, transverse slots so positioned that the mid-section of each slot is disposed on only one side of the unbent stylet's longitudinal centerline, away from the electrical wires, thereby minimizing their exposure to the slots, each of which is squeezed so as to narrow its width, closing it to a degree, whenever the stylet is flexed.

Means for tensioning the flexible wire includes the bell crank which is pivotally mounted on a forked structure situated at the stylet holder's terminal end distal from the cylindrically-shaped void. The forked structure, which defines a U-shaped channel with opposing side walls, generally straddles the bell crank's short arm to which the flexible wire is affixed. By rotating the bell crank's trigger arm toward the stylet holder and, in the process, simultaneously moving the short arm away from the through passageway and its opening into the U-shaped channel—an opening which is located approximately midway between the opposing side walls, one can pull a short portion of the flexible wire outwardly from the through passageway, thereby reducing, while the trigger arm is so rotated, the length of the flexible wire retained within the tubular element and flexing the stylet. Moreover, the further the trigger arm is rotated in a direction toward the stylet holder so as to bring the trigger arm's longitudinal centerline more nearly into generally parallel alignment with the path which the flexible wire takes, under tension, between the through passageway's respective junctures with the cylindrically-shaped void and the U-shaped channel, the greater is the flexing of the stylet.

In order for the improved endo-tracheal device to be operable using only one hand, spacing between the bell crank's axis of rotation and an elongated portion of the stylet holder which extends for most of its length and which has a generally cylindrically-shaped exterior is preferably such that the trigger arm not only clears said portion but also is narrow enough that the average medical practitioner can simultaneously grasp such portion and use the finger(s) of his grasping hand to rotate the trigger arm-throughout its full range of motion.

DETAILED DESCRIPTION OF THE PREFERRED EMBODIMENT

In the drawings, an improved endo-tracheal intubation device is indicated generally by the reference numeral 10. The device 10, designed for single use only, provides its own bright, battery-powered LED light 18 to illuminate the vocal cords of a patient's larynx so that a medical practitioner can visualize them directly in certain individuals—specifically, those whose neck can be hyper-extended in such a fashion that anatomical structures along the patient's airway are aligned linearly—and, more generally, to enable a trained observer to confirm placement of a conventional endo-tracheal tube 40 in the trachea, as can be determined by observing the position of the device's light as it shines through the skin of the patient's neck. Coupled with this low cost visualization tool is a novel mechanism which allows the operator to deflect the tip of the endotracheal tube 40 towards the vocal cords, thereby facilitating its proper placement anteriorly in the trachea.

Figure 5:
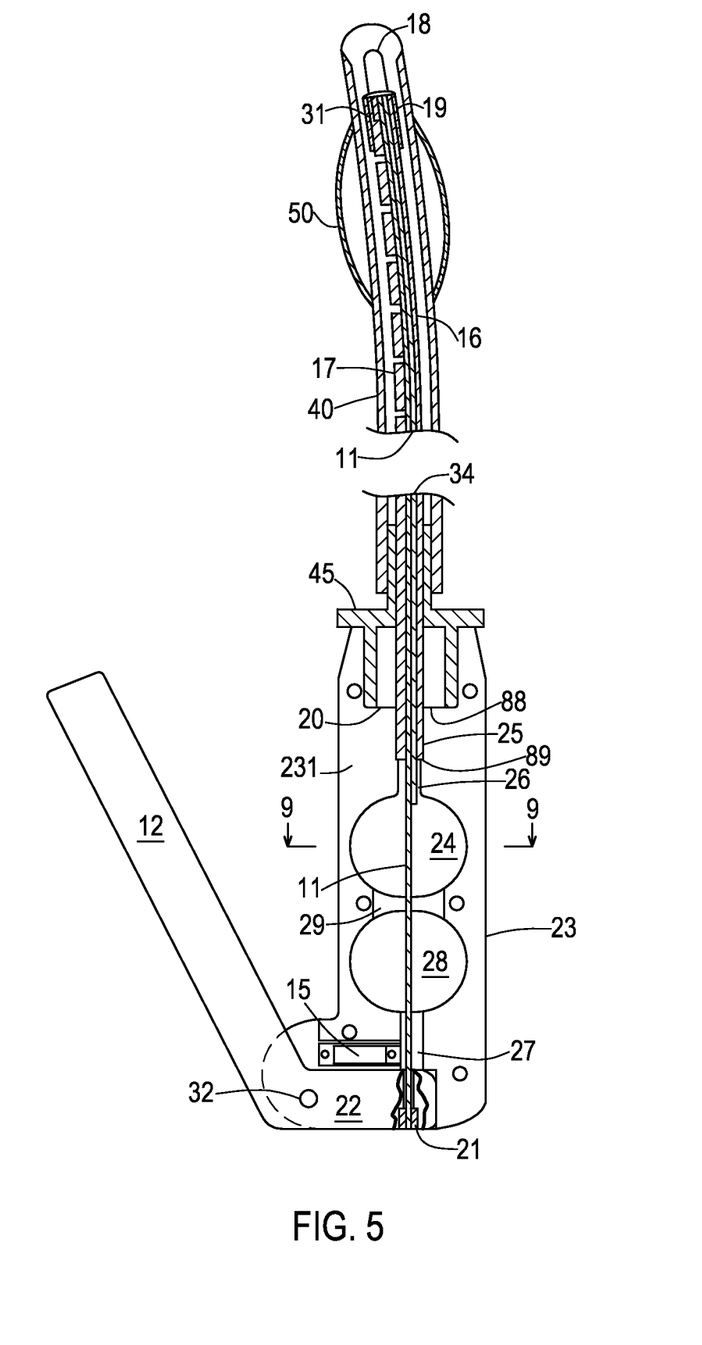
FIGS. 5 depicts, on an enlarged scale, components of the endo-tracheal device according to FIG. 4, showing, (i) the first flat wall surface of the first element, of the stylet holder, (ii) the bell crank pivotally mounted on the first element, (iii) a cross-sectional view of the stylet, (iv) a cross-sectional view of the endotracheal tube, and of (v) a cut-out cross-sectional view of the flexible wire connected to the bell crank's short arm as viewed along line 5-5 shown in FIG. 4.

Basic to the device 10 is a stylet having a substantially tubular element 16 (FIGS. 1-3, 5 and 13). Fabricated of a hollow, semi-rigid, medical grade plastic material which is generally circular in transverse cross-section, the tubular element 16 preferably measures, at most, approximately 6.0 mm in diameter in order to ease its insertion, while encased in the tube 40, between the vocal cords. So that the tip of the tube 40 can be deflected towards the vocal cords, the tubular element 16 defines a scored section 11 which can be bent in a controlled manner by tensioning a flexible wire 11 (FIGS. 1-3 and 5). As is best illustrated in FIG. 5, the tubular element 16 encases a portion of the flexible wire 11 which not only extends lengthwise through it but also protrudes therefrom.

Figure 1:
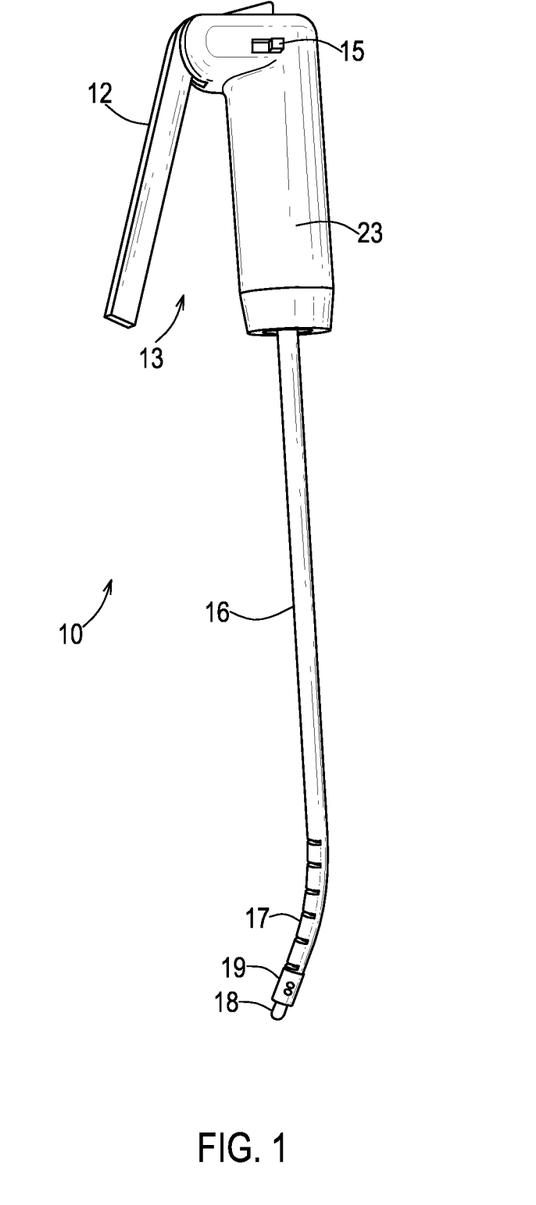
FIG. 1 is a perspective view of the endo-tracheal intubation device according to the present invention, showing its tubular stylet in a generally unflexed condition, with the trigger arm of the device's bell crank rotated outwardly.
Figure 2:
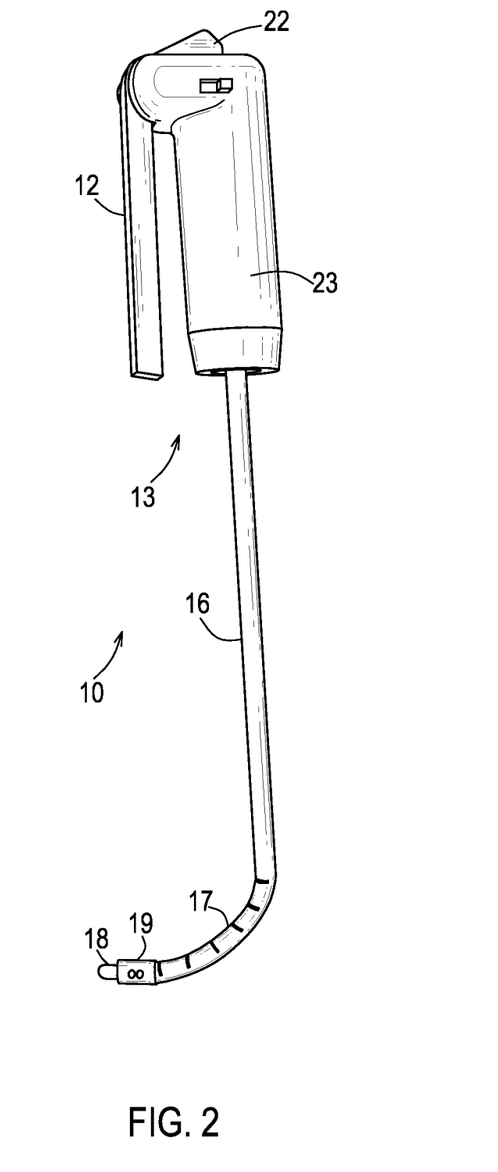
FIG. 2 is a perspective view of the endo-tracheal intubation device according to FIG. 1, showing its tubular stylet in a bent configuration.
Figure 3:
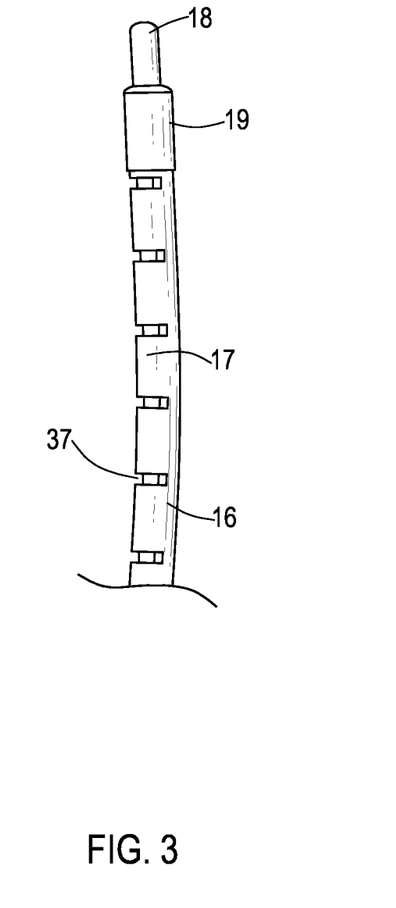
FIG. 3 is a perspective view, on an enlarged scale, of a fragmentary portion of the endo-tracheal intubation device according to FIG. 1, showing the end of its stylet distal from its holder.
Figure 12:
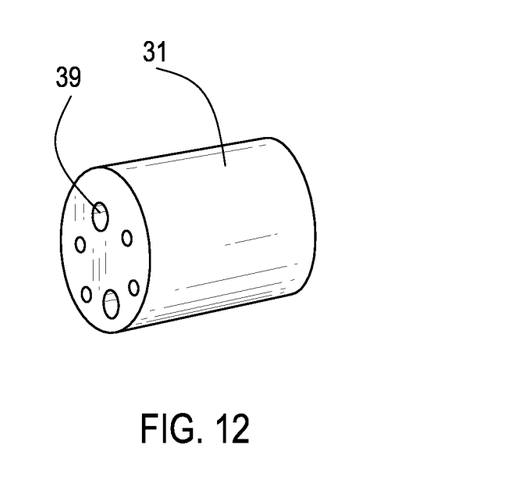
FIG. 12 is a perspective view, on an enlarged scale, of a disk onto which the steering wire is attached, the disk being part of the stylet in the endo-tracheal intubation device according to FIG. 5.

The scored section 17 itself defines a plurality of spaced apart, transverse slots 37 so positioned that the midsection of each slot is disposed on only one side of the unbent stylet's longitudinal centerline, away from electrical wires 34 which connect the LED light 18, mounted on a disk 31 at the stylet's tip, to batteries 14 (FIGS. 3, 5 and 12). Preferably, the spacing between the elongated edges of each individual slot 37, when the stylet is not in a state of flexure, measures, by way of example, approximately 1.5 mm; and the length of each segment of the tubular element 16 which separates proximal edges of each contiguous pair of slots 37 is typically about 7.9 mm, giving the scored section 17, in a tubular element 16 with a diameter of approximately 4.7 mm, an overall length of about 48.5 mm.

Figure 6:
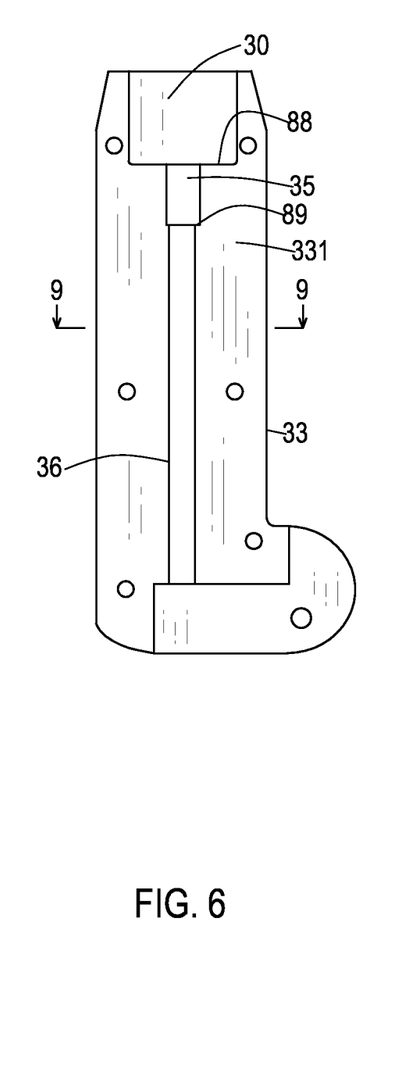
FIG. 6 depicts a view of the second flat wall surface of the second element of the stylet holder.
Figure 7:
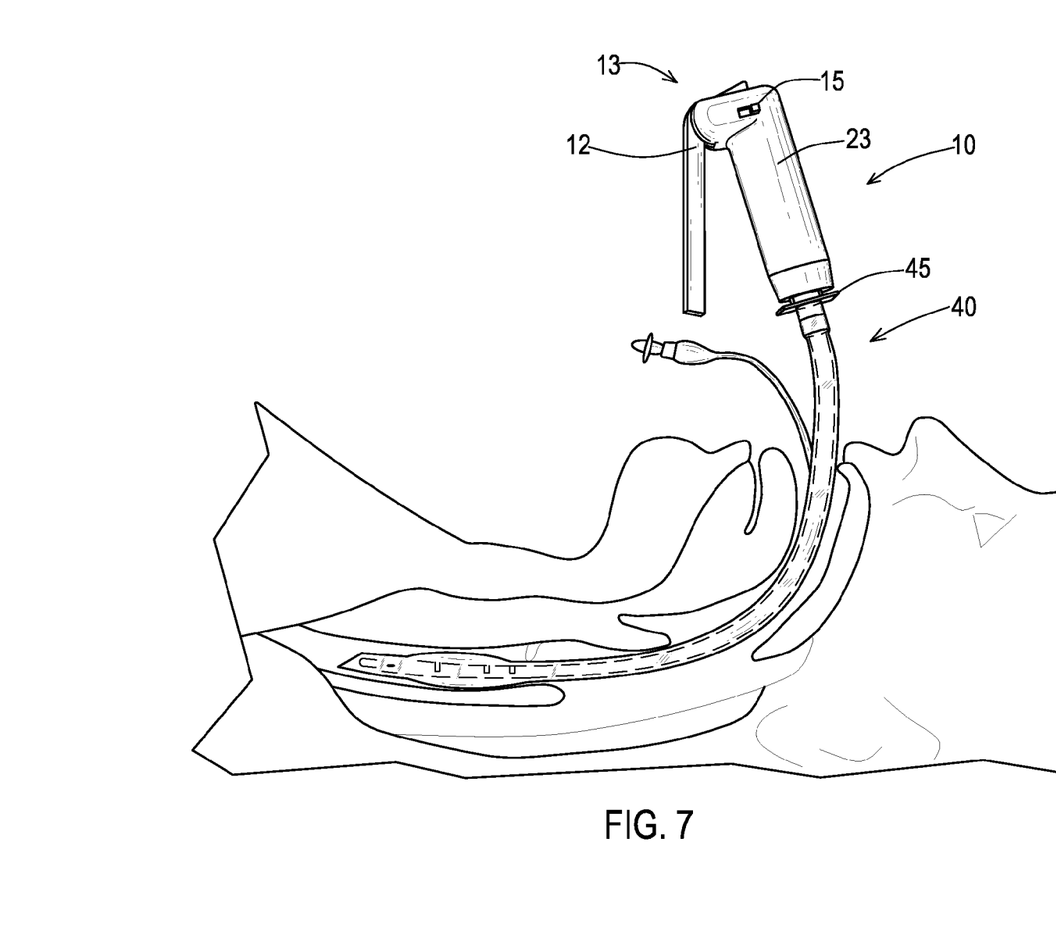
FIG. 7 shows a view of the endo-tracheal intubation device according to FIG. 4 successfully placed orally into a patient's trachea.
Figure 8:
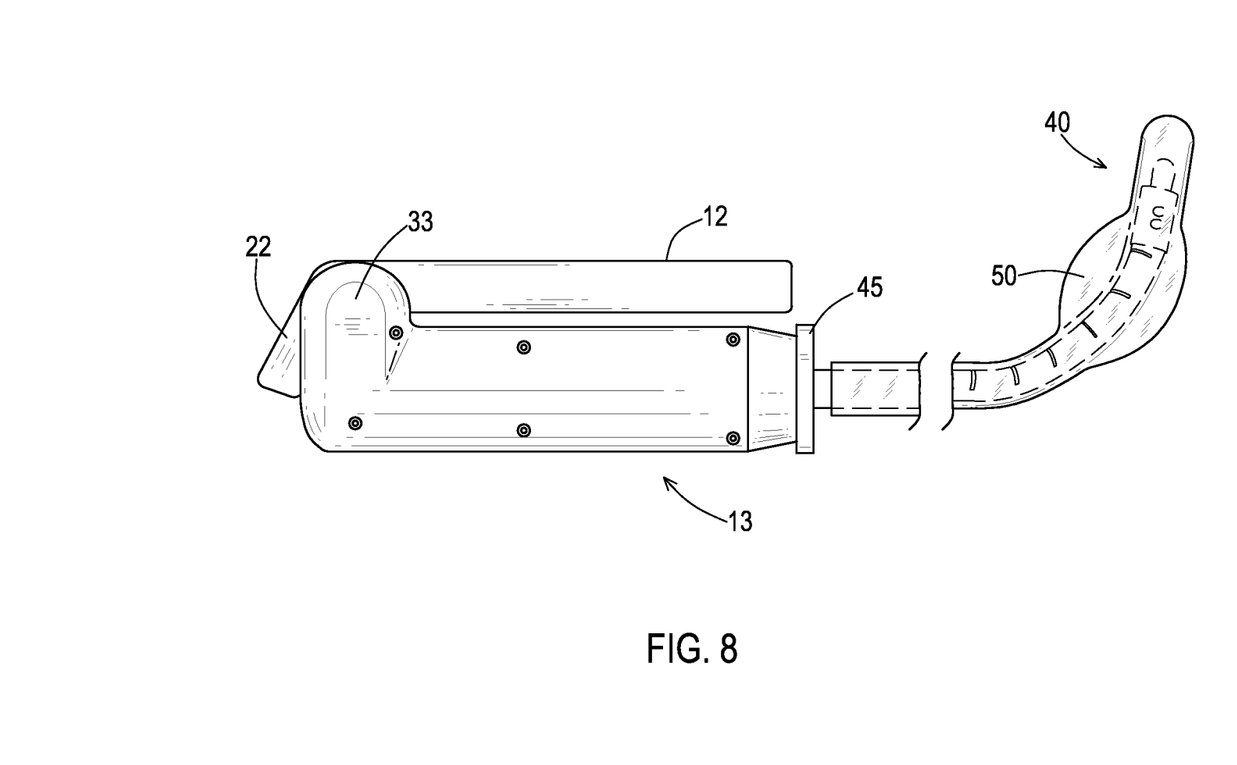
FIG. 8 is a side elevation view, on an enlarged scale, of fragmentary portions of the endo-tracheal intubation device according to FIG. 1, with its tubular stylet in a bent configuration and encased in an endo-tracheal tube.
Figure 9:
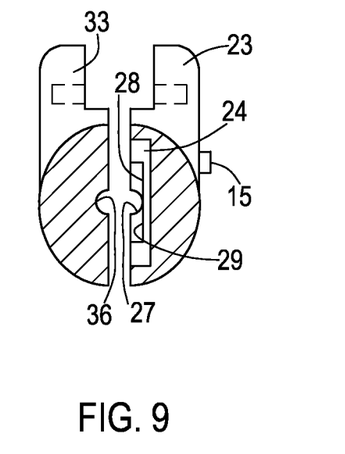
FIG. 9 is a transverse cross-sectional view of the first and second elements, taken along line 9-9 shown in FIGS. 5 and 6, respectively, with the first and second elements of the stylet holder being positioned apart from one another.
Figure 10:
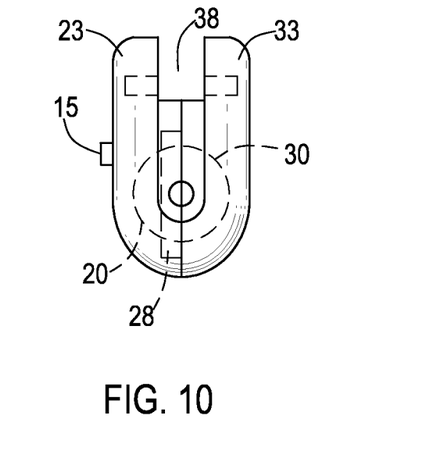
FIG. 10 is an end elevation view of the stylet holder, without the bell crank pivotally mounted thereon.
Figure 13:
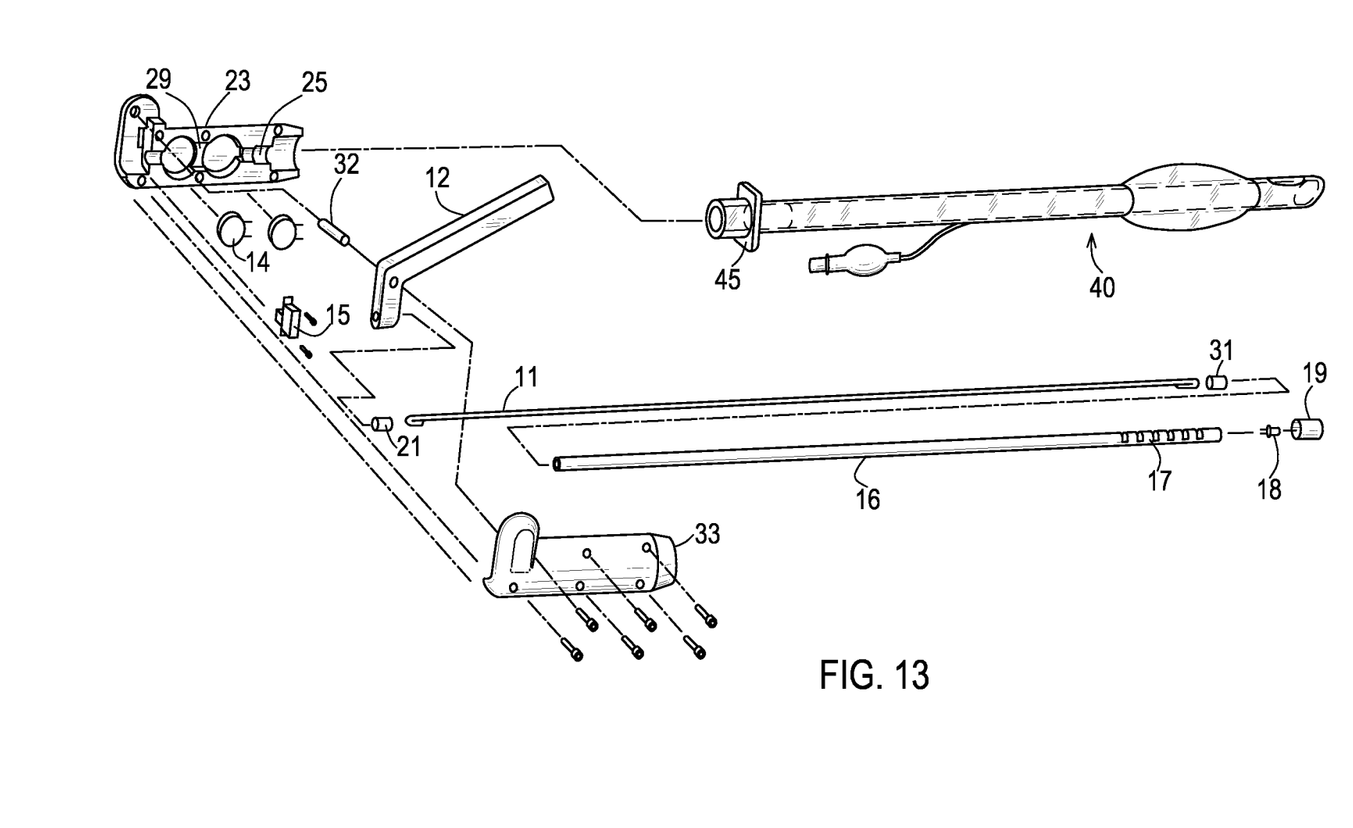
FIG. 13 is an exploded view, on a reduced scale, of the endo-tracheal intubation device according to FIG. 1 and of an endo-tracheal tube having an adapter mountable on the stylet holder.

Also included in the device 10 is a stylet holder 13 which has two major components: a first element 23 and a second element 33 which, except for structures defined by the first element 23 to accommodate the batteries 14 and an on-and-off switch 15, are generally mirror images of each other (FIGS. 5, 6 and 13). Generally flat first and second walls, namely, first wall 231 and second wall 331, each of which is interrupted by a plurality of interconnected recesses which divide it into two parts along its entire length, extend longitudinally across the first and second elements 23 and 33, respectively (see, FIGS. 5 and 6). These interconnected recesses, when the elements 23, 33 are fastened together in assembled relation, define a pair of contiguous first and second cylindrically-shaped voids 20/30 and 25/35 and a through passageway 26/36 extending generally longitudinally from its juncture with the second cylindrically-shaped void 25/35 to the passageway's opening into a U-shaped channel 38, which is defined by open-ended cutouts in the elements 23, 33 (see FIGS. 5, 6, 9, 10, and 13). The interconnected recesses, in the case of the first element 23, include concavities 20, 25, 26 and 27, each of which is approximately semicircular in transverse cross-section, as well as battery compartments 24, 28 and a shallow cutout 29 juxtaposed between them. Similarly, the interconnected concavities 30, 35 and 36 in the second element 33 are also approximately semi-circular in transverse cross-section, with the radius of curvature of each of the concavities in the first element 23 and the concavity in the second element with which, in assembled relation, it is paired having the same radius of curvature. Moreover, paired concavities 20, 30 have a radius of curvature which is greater than that of paired concavities 25, 35, thereby creating a first shoulder 88 between the first and second cylindrically-shaped voids 20/30 and 25/35. Likewise, paired concavities 25, 35 have a greater radius of curvature than do paired concavities 26, 36, so that a second shoulder 89 is formed at the juncture between the second cylindrically-shaped void 25/35 and the through passageway 26/36 (see, FIGS. 5 and 6).

Abutting the second shoulder in the assembled holder 13 is one end of the tubular element 16. Preferably during assembly, said end is slideably slip-fitted into the concavity 25 until the tubular element 16 abuts the juncture between concavities 25, 26. Next, in preparation for its being affixed to tensioning means located distal from the concavity 25, the protruding portion of the flexible wire 11 is stretched across the interconnected recesses in the first element 23. By following this procedure, the assembler can then simultaneously pinch the tubular element 16 between concavities 25, 35, holding it in place within the second cylindrically-shaped void, and position the protruding portion of the flexible wire 11 so that it traverses the through passageway and extends outwardly therefrom into the U-shaped channel 38.

Figure 11:
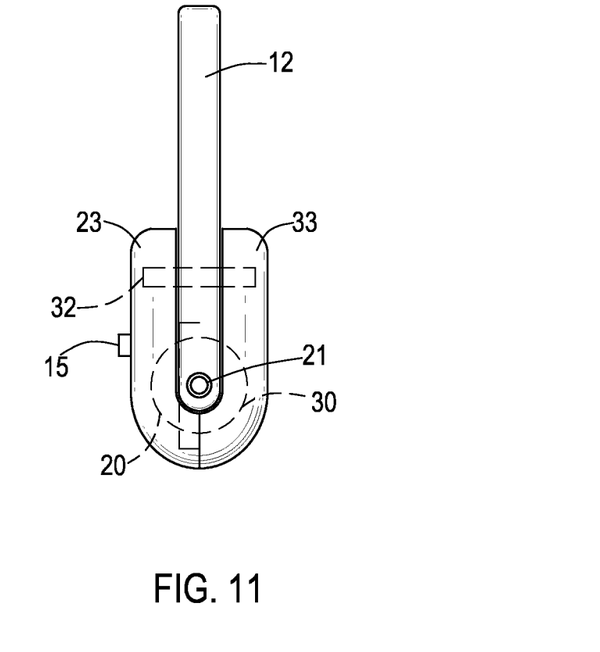
FIG. 11 is an end elevation view of the stylet holder and of the bell crank pivotally mounted thereon.

Means for tensioning the flexible wire 11 includes a bell crank pivotally mounted, with the use of a pin 32, to the first and second elements 23, 33 at their respective ends located distally from the first and second cylindrically-shaped voids in the assembled holder (FIGS. 5, 6 and 11). Attached to the bell crank's short arm 22 by first inserting the wire 11 through a narrow hole formed therein, pulling the wire taut and lastly affixing a metal sleeve 21 thereto so as to secure the sleeve/flexible wire juncture within the narrow hole, the wire 11 can then be tensioned by rotating the bell crank's trigger arm 12 toward the holder 13—a process which simultaneously moves the short arm 22 away from the through passageway, as well as its opening into the U-shaped channel 38, and pulls a short portion of the wire 11 outwardly, thereby reducing, while the trigger arm is so rotated, the length of the flexible wire retained within the tubular element 16 and flexing the stylet. As can be seen in FIGS. 1, 2, 5, 7 and 8, the further the trigger arm 12 is rotated in a direction toward the holder 13, the greater is the flexing of the stylet's scored section 17.

Distal from the stylet holder 13, the end of the flexible wire 11 is preferably looped through holes 39 defined by the disk 31, so as to affix the wire 11 thereto. As illustrated in FIGS. 3, 5 and 13, both the disk 31 and a portion of the tubular element 16 contiguous with the disk are covered by a stainless cap 19 from which the LED light 18 protrudes outwardly at the stylet's tip.

Figure 4:
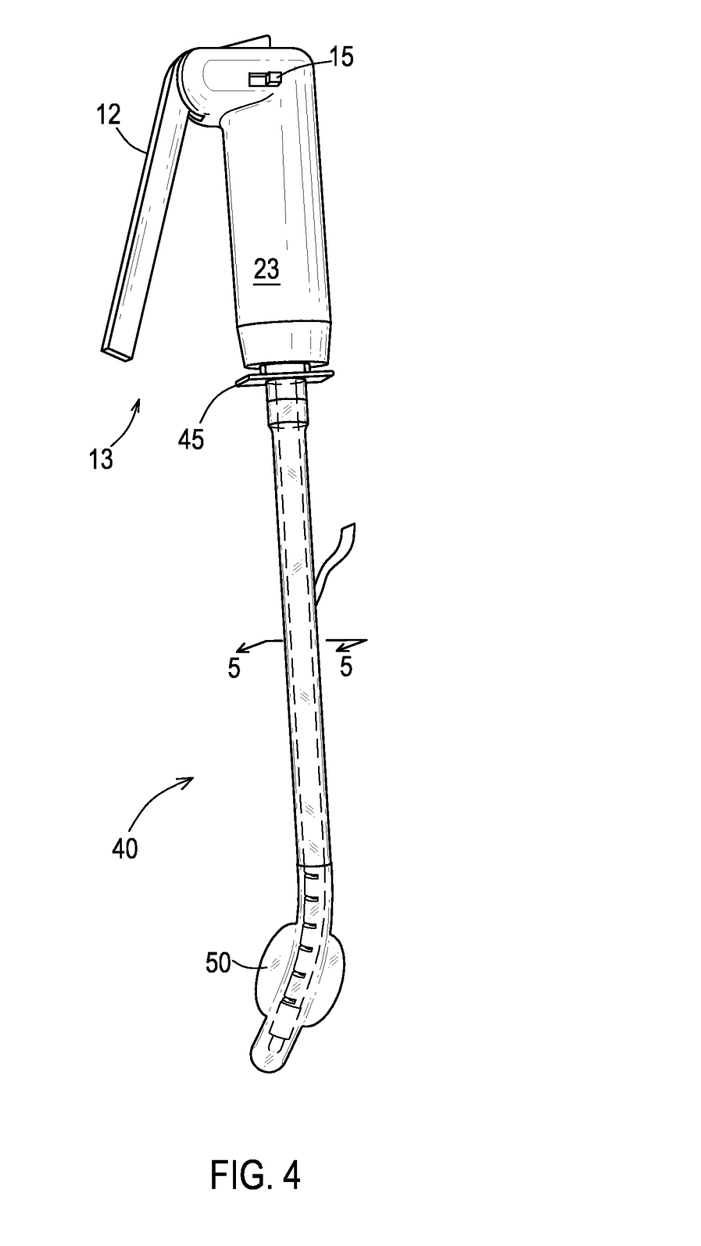
FIG. 4 is a perspective view of the endo-tracheal intubation device according to FIG. 1, showing its stylet encased in an endo-tracheal tube adaptively mounted on the stylet holder.

Prior to use, the stylet, with its tubular element 16 mounted within the holder's second cylindrically-shaped void, is inserted into an endo-tracheal tube 40 fitted with a conventional adapter 45; and the latter is then slip-fitted into the holder's first cylindrically-shaped void, thereby encasing the stylet within the tube (FIG. 4).

During use of this combination endo-tracheal tube/adjustably bendable stylet assembly, the device 10 can be employed to maneuver the tip of its stylet, as well as the overall tip of said assembly past a patient's tongue and inbetween his vocal cords. After the latter tip has been inserted past them, the bell crank's trigger arm 12, if previously engaged, may be released, reducing substantially all of the tension on the flexible wire 11 and relaxing the stylet's bent configuration, while said assembly is then inserted further into the patient's airway. Once the assembly is properly placed anteriorly into the trachea, the endo-tracheal tube's balloon cuff 50 is inflated, locking the tube 40 in place; and the stylet is withdrawn, allowing the patient to breathe/be ventilated.

Because of the brightness of the LED light 18, a trained observer can confirm placement of the tube 40 in the trachea, even under emergency field conditions and in bright sunlight, or in a well-lighted room, by placing a dark coyer (not shown) over the patient's neck. With the dark cover so placed, the operator can then visualize the position of said assembly's tip because of the skin illumination of the anterior aspect of the neck which the LED light 18 provides.

Other advantages of the improved endo-tracheal intubation device 10 include its affordability. In the preferred embodiment, the stylet holder 13 and the bell crank are fabricated from surgical grade plastics; but they can also be made from a variety of materials, so that device 10 is inexpensive to manufacture. Thus, it is suitable for single patient use only and fills the need for affordable devices which can perform the function of much more costly devices without compromising the quality of patient care.

What is claimed:

1. An endo-tracheal intubation device comprising:
    a stylet comprising:
        a stylet tubular element having a stylet distal end and a stylet proximal end opposite said stylet distal end,
        a stylet channel extending through said tubular element from said stylet distal end to said stylet proximal end, and
        a scored section proximate said stylet distal end, said scored section comprising a plurality of spaced apart transverse slots positioned along and extending into one side of said stylet tubular element;
    a stylet holder comprising:
        a stylet holder distal end and a stylet holder proximal end opposite said stylet holder distal end, a cavity extending into and within said stylet holder distal end of said stylet holder, said cavity sized so as to receive said stylet proximal end of said stylet, a U-shaped channel along said stylet holder proximal end, and a through passageway extending from said cavity into said U-shaped channel, a bell crank pivotally connected to said stylet holder proximal end, said bell crank comprising:

a short arm positioned so as to pivotably move within said U-shaped channel, and an elongated trigger arm disposed at an obtuse angle to said short arm, said elongated trigger arm being pivotably movable towards and away from an outer surface of said stylet holder; and a flexible wire comprising:

a continuous wire having a first wire end and a second wire end opposite said first wire end, said first wire end being connected to said stylet, and said second wire end being connected to said short arm, said flexible wire extending through said stylet channel along said scored section, beyond said stylet proximal end into said stylet holder and through said through passageway so as to connect said stylet to said short arm;

wherein movement of said elongated trigger arm towards said outer surface of said stylet holder causes said stylet to bend along said scored section, and wherein said cavity of said stylet holder comprises (i) a first cavity portion at said stylet holder distal end, (ii) a second cavity portion between said first cavity portion and said through passageway, said first cavity portion having a greater cross-sectional area than said second cavity portion, (iii) a first shoulder between said first cavity portion and said second cavity portion, and (iv) a second shoulder positioned between said second cavity portion and said through passageway.

2. The endo-tracheal intubation device of claim 1, wherein said stylet tubular element comprises a single continuous tubular member such that tubular member portions located between said plurality of spaced apart transverse slots share an outer surface along said stylet tubular element.

3. The endo-tracheal intubation device of claim 1, wherein said stylet further comprises a light at said stylet distal end, and said stylet holder comprises a switch that cuts on and off said light.

4. The endo-tracheal intubation device of claim 3, wherein said light forms a tip of said stylet at said stylet distal end.

5. The endo-tracheal intubation device of claim 3, further comprising an electrically conductive wire connecting said light to said switch.

6. The endo-tracheal intubation device of claim 1, wherein said stylet holder further comprises (i) at least one battery compartment within an inner volume of said stylet holder, and (ii) a battery positioned within each battery compartment.

7. The endo-tracheal intubation device of claim 1, wherein said stylet holder comprises first and second elements that join together to form a housing of said stylet holder, each of said first and second elements having corresponding mirror-image features so as to form (i) said cavity, (ii) said U-shaped channel, and (iii) said through passageway when assembled with one another.

8. The endo-tracheal intubation device of claim 1, wherein said stylet proximal end of said stylet engages with said second cavity portion.

9. The endo-tracheal intubation device of claim 8, further comprising:

an endo-tracheal tube having an endo-tracheal tube distal end and an endo-tracheal tube proximal end opposite said endo-tracheal tube distal end.

10. The endo-tracheal intubation device of claim 9, wherein said tube proximal end of said endo-tracheal tube engages with said first cavity portion.

11. An endo-tracheal intubation device comprising:

a stylet comprising:

a stylet tubular element having a stylet distal end and a stylet proximal end opposite said stylet distal end, a stylet channel extending through said tubular element from said stylet distal end to said stylet proximal end, a scored section proximate said stylet distal end, said scored section comprising a plurality of spaced apart transverse slots positioned along and extending into one side of said stylet tubular element, and a light forming a tip of said stylet at said stylet distal end;

a stylet holder comprising:

a stylet holder distal end and a stylet holder proximal end opposite said stylet holder distal end, a cavity extending into and within said stylet holder distal end of said stylet holder, said cavity sized so as to receive said stylet proximal end of said stylet, a U-shaped channel along said stylet holder proximal end, a through passageway extending from said cavity into said U-shaped channel, (i) at least one battery compartment within an inner volume of said stylet holder, and (ii) a battery positioned within each battery compartment, and electrical circuitry extending from each battery to a switch that cuts on and off said light;

a bell crank pivotally connected to said stylet holder proximal end, said bell crank comprising:

a short arm positioned so as to pivotably move within said U-shaped channel, and an elongated trigger arm disposed at an obtuse angle to said short arm, said elongated trigger arm being pivotably movable towards and away from an outer surface of said stylet holder;

a flexible wire comprising:

a continuous wire having a first wire end and a second wire end opposite said first wire end, said first wire end being connected to said stylet, and said second wire end being connected to said short arm, said flexible wire extending through said stylet channel along said scored section, beyond said stylet proximal end into said stylet holder and through said through passageway so as to connect said stylet to said short arm; and an electrically conductive wire connecting said light to said switch;

wherein (I) movement of said elongated trigger arm towards said outer surface of said stylet holder causes said stylet to bend along said scored section, (II) said stylet holder comprises first and second elements that join together to form a housing of said stylet holder, each of said first and second elements having corresponding mirror-image features so as to form (i) said cavity, (ii) said U-shaped channel, and (iii) said through passageway when assembled with one another, and (III) said cavity of said stylet holder comprises (i) a first cavity portion at said stylet holder distal end, (ii) a second cavity portion between said first cavity portion and said through passageway, said first cavity portion having a greater cross-sectional area than said second cavity portion, (iii) a first shoulder between said first cavity portion and said second cavity portion, and (iv) a second shoulder positioned between said second cavity portion and said through passageway.

12. The endo-tracheal intubation device of claim 11, wherein said stylet proximal end of said stylet extends into and engages with said second cavity portion such that an annular portion of said first cavity portion extends around an outer surface of said stylet, and said second shoulder prevents said stylet from extending into said through passageway.

13. The endo-tracheal intubation device of claim 12, further comprising:
an endo-tracheal tube having a an endo-tracheal tube distal end and an endo-tracheal tube proximal end opposite said endo-tracheal tube distal end, said endo-tracheal tube proximal end of said endo-tracheal tube extending into and engaging with said first cavity portion, and said first shoulder prevents said endo-tracheal tube proximal end from extending into said second cavity portion.

14. An endo-tracheal intubation device comprising:
a stylet comprising:
  a stylet tubular element having a stylet distal end, a stylet proximal end opposite said stylet distal end, and a stylet cross-sectional area at said stylet proximal end,
  a stylet channel extending through said tubular element from said stylet distal end to said stylet proximal end, and
  a scored section proximate said stylet distal end, said scored section comprising a plurality of spaced apart transverse slots positioned along and extending into one side of said stylet tubular element;
a stylet holder comprising:
  a stylet holder distal end and a stylet holder proximal end opposite said stylet holder distal end,
  a cavity extending into and within said stylet holder distal end of said stylet holder, said cavity sized so as to receive said stylet proximal end of said stylet, said cavity comprising (i) a first cavity portion at said stylet holder distal end, (ii) a second cavity portion between said first cavity portion and said stylet holder proximal end, said first cavity portion having a greater cross-sectional area than said second cavity portion, and said second cavity portion having a cross-sectional area substantially equal to said stylet cross-sectional area at said stylet proximal end, (iii) a first shoulder between said first cavity portion and said second cavity portion, and (iv) a second shoulder positioned at said second cavity portion opposite said first cavity portion,
  a U-shaped channel along said stylet holder proximal end, and
  a through passageway extending from said cavity into said U-shaped channel, said through passageway having a cross-sectional area that is less than a cross-sectional area of said second cavity portion,
a bell crank pivotally connected to said stylet holder proximal end, said bell crank comprising:
  a short arm positioned so as to pivotably move within said U-shaped channel, and
  an elongated trigger arm disposed at an obtuse angle to said short arm, said elongated trigger arm being pivotably movable towards and away from an outer surface of said stylet holder; and
a flexible wire comprising:
  a continuous wire having a first wire end and a second wire end opposite said first wire end,
  said first wire end being connected to said stylet, and
  said second wire end being connected to said short arm, said flexible wire extending through said stylet channel along said scored section, beyond said stylet proximal end into said stylet holder and through said through passageway so as to connect said stylet to said short arm;
wherein movement of said elongated trigger arm towards said outer surface of said stylet holder causes said stylet to bend along said scored section.

15. The endo-tracheal intubation device of claim 14, wherein said stylet holder comprises first and second elements that join together to form a housing of said stylet holder, each of said first and second elements having corresponding mirror-image features so as to form (i) said cavity, (ii) said U-shaped channel, and (iii) said through passageway when assembled with one another.

16. The endo-tracheal intubation device of claim 15, wherein said stylet further comprises a light at said stylet distal end, and said stylet holder comprises a switch that cuts on and off said light.

17. The endo-tracheal intubation device of claim 1, wherein (i) said stylet tubular element has a stylet cross-sectional area at said stylet proximal end, (ii) said second cavity portion has a cross-sectional area substantially equal to said stylet cross-sectional area at said stylet proximal end, and (iii) said through passageway has a cross-sectional area that is less than a cross-sectional area of said second cavity portion.

18. The endo-tracheal intubation device of claim 11, wherein (i) said stylet tubular element has a stylet cross-sectional area at said stylet proximal end, (ii) said second cavity portion has a cross-sectional area substantially equal to said stylet cross-sectional area at said stylet proximal end, and (iii) said through passageway has a cross-sectional area that is less than a cross-sectional area of said second cavity portion.

19. The endo-tracheal intubation device of claim 13, wherein said endo-tracheal intubation device consists of said stylet, said stylet holder, said bell crank, said flexible wire, said electrically conductive wire connecting said light to said switch, and said endo-tracheal tube.

20. The endo-tracheal intubation device of claim 16, further comprising:
an endo-tracheal tube having an endo-tracheal tube distal end and an endo-tracheal tube proximal end opposite said endo-tracheal tube distal end, said endo-tracheal tube proximal end of said endo-tracheal tube extending into and engaging with said first cavity portion, and said first shoulder prevents said endo-tracheal tube proximal end from extending into said second cavity portion.

* * * * *